(12) United States Patent
Nuccitelli et al.

(10) Patent No.: US 10,905,874 B2
(45) Date of Patent: *Feb. 2, 2021

(54) NANOSECOND PULSED ELECTRIC FIELDS CAUSE MELANOMAS TO SELF-DESTRUCT

(71) Applicants: Eastern Virginia Medical School, Norfolk, VA (US); Old Dominion University Research Foundation, Norfolk, VA (US)

(72) Inventors: Richard Nuccitelli, Norfolk, VA (US); Stephen J. Beebe, Norfolk, VA (US); Karl H. Schoenbach, Norfolk, VA (US)

(73) Assignees: Eastern Virginia Medical School, Norfolk, VA (US); Old Dominion University Research Foundation, Norfolk, VA (US)

( * ) Notice: Subject to any disclaimer, the term of this patent is extended or adjusted under 35 U.S.C. 154(b) by 419 days.

This patent is subject to a terminal disclaimer.

(21) Appl. No.: 15/922,758

(22) Filed: Mar. 15, 2018

(65) Prior Publication Data

US 2018/0200510 A1   Jul. 19, 2018

Related U.S. Application Data

(63) Continuation of application No. 14/869,286, filed on Sep. 29, 2015, now Pat. No. 9,943,684, which is a (Continued)

(51) Int. Cl.
*A61N 1/20* (2006.01)
*A61N 1/32* (2006.01)

(52) U.S. Cl.
CPC ............. *A61N 1/205* (2013.01); *A61N 1/327* (2013.01)

(58) Field of Classification Search
CPC .......... A61B 18/12; A61B 2018/00613; A61B 2018/00577; A61B 2018/1467;
(Continued)

(56) References Cited

U.S. PATENT DOCUMENTS 6,326,177 B1 * 12/2001 Schoenbach ............. A61P 3/04
435/173.7
7,655,004 B2 * 2/2010 Long .................. A61B 18/1482
606/37

(Continued)

FOREIGN PATENT DOCUMENTS

WO   WO-2005032646   4/2005

OTHER PUBLICATIONS

Albarenque et al., "T-2 toxin-induced apoptosis in rat keratinocyte primary cultures," Experimental and Molecular Pathology, 78, pp. 144-149 (2005).

(Continued)

*Primary Examiner* — Michael F Peffley
(74) *Attorney, Agent, or Firm* — Wilmer Cutler Pickering Hale and Dorr LLP

(57) ABSTRACT

Methods for a new, drug-free therapy for treating solid skin tumors through the application of nanosecond pulsed electric fields ("nsPEFs") are provided. In one embodiment of the invention, the cells are melanoma cells, and the applied nsPEFs penetrate into the interior of tumor cells and cause tumor cell nuclei to rapidly shrink and tumor blood flow to stop. This new technique provides a highly localized targeting of tumor cells with only minor effects on overlying skin.

25 Claims, 13 Drawing Sheets

Related U.S. Application Data continuation of application No. 12/280,280, filed as application No. PCT/US2007/004844 on Feb. 26, 2007, now Pat. No. 9,168,373.

(60) Provisional application No. 60/776,215, filed on Feb. 24, 2006.

(58) Field of Classification Search
CPC ...... A61B 2018/126; A61B 2018/0016; A61B 2018/00452; A61N 1/205; A61N 1/327
See application file for complete search history.

(56) References Cited

U.S. PATENT DOCUMENTS

| | | | | |
|---|---|---|---|---|
| 7,680,543 | B2* | 3/2010 | Azure | A61B 18/1477 606/41 |
| 8,048,067 | B2* | 11/2011 | Davalos | A61B 18/1233 606/32 |
| 2002/0010491 | A1* | 1/2002 | Schoenbach | A61B 18/1206 607/2 |
| 2005/0288730 | A1* | 12/2005 | Deem | A61N 1/205 607/42 |

OTHER PUBLICATIONS

Beebe et al., "Nanosecond, high-intensity pulsed electric fields induce apoptosis in human cells," The FASEB Journal, 17(11), pp. 1493-1495 (2003).

Beebe, "nsPEF-Induced Cell Effects," DNA and Cell Biology, 22(12), ISSN 1044-5498, pp. 795-796 (2003).

Beebe et al., "Nanosecond Pulsed Electric Field (nsPEF) Effects on Cells and Tissues: Apoptosis Induction and Tumor Growth Inhibition," IEEE Transactions on Plasma Science, 30(1), pp. 286-292 (2002).

Beebe et al., "Nanosecond pulsed electric fields modulate cell function through intraceulluar signal transduction mechanisms," Physiol. Meas., 25, pp. 1077-1093 (2004).

Buescher et al., "Effects of Submicrosecond, High Intensity Pulsed Electric Fields on Living Cells—Intracellular Electromanipulation," IEEE Transactions on Dielectrics and Electrical Insulation, 10(5), pp. 789-794 (2003).

Buescher et al., "Submicrosecond Intense Pulsed Electric Field Effects on Intracellular Free Calcium: Mechanisms and Effects," IEEE Transactions on Plasma Science, 32(4), pp. 1563-1572 (2004).

Chen et al., "Leukemic cell intracellular responses to nanosecond electric fields," Biochemical and Biophysical Research Communications, 317, 421-427 (2004).

Deng et al., "The Effects of Intense Submicrosecond Electrical Pulses on Cells," Biophysical Journal, 84, pp. 2709-2714 (2003).

Gothelf et al., "Electrochemotherapy: results of cancer treatment using enhanced delivery of bleomycin by electroporation," Cancer Treatment Reviews 29, pp. 371-387 (2003).

Gruenbaum et al., "The Nuclear Lamina Comes of Age," Nature Reviews, Molecular Cell Biology, 6, pp. 21-31 (2005).

Haemmerich et al., "Thermal tumour ablation: Devices, clinical applications and future directions," Int. J. Hyperthermia, 21(8), pp. 755-760 (2005).

Hu et al., "Simulations of transient membrane behavior in cells subjected to a high-intensity ultrashort electric pulse," Physical Review E, 71, pp. 031914-1 to 031914-9 (2005).

Joshi et al., "Theoretical predictions of electromechanical deformation of cells subjected to high voltages for membrane electroporation," Physical Review E, vol. 65, pp. 021913-1 to 021913-10 (2002).

Kolb et al., "Nanosecond Pulsed Electric Field Generators for the Study of Subcellular Effects," Bioelectromagnetics, 27, pp. 172-187 (2006).

Kubota et al., "A case of perineal malignant melanoma successfully treated with electrochemotherapy," Melanoma Research, 15, pp. 133-134 (2005).

Lucas et al., "IL-12 Gene Therapy Using an Electrically Mediated Nonviral Approach Reduces Metastatic Growth of Melanoma," DNA and Cell Biology, 22(12), pp. 755-763 (2003).

Mankowski, "A Review of Short Pulse Generator Technology," IEEE Transaction on Plasma Science, 28(1), pp. 102-108 (2000).

Nuccitelli et al., "A New Pulsed Electric Field Therapy for Melanoma Disrupts the Tumor's Blood Supply and Causes Complete Remission without Recurrence", Int. J. Cancer, 125, pp. 438-445 (2009).

Parvathenani et al., "Type I cAMP-dependent Protein Kinase Delays Apoptosis in Human Neutrophils at a Site Upstream of Caspase-3," The Journal of Biological Chemistry, 273(12), pp. 6736-6743 (1998).

International Search Report for International Application No. PCT/US07/04844, dated Dec. 14, 2007 (3 pages).

Schoenbach et al., "Intracellular Effect of Ultrashort Electrical Pulses," Bioelectromagnetics, 22, pp. 440-448 (2001).

Sersa et al., "Tumour Blood Flow Changes Induced by Application of Electric Pulses," European Journal of Cancer, 35(4), pp. 672-677 (1999).

Stacey et al., "Differential effects in cells exposed to ultra-short, high intensity electric fields: cell survival, DNA damage, and cell cycle analysis," Mutation Research, 542, pp. 65-75 (2003).

Tanabe et al., "Radiofrequency Ablation," Cancer, 100(3), pp. 641-650 (2003).

Teissie et al., "Mechanisms of cell membrane electropermeabilisation: A minireview of our present (lack of?) knowledge," Biochimica et Biophysica Acta, 1724, pp. 270-280 (2005).

Vernier et al., "Calcium bursts induced by nanosecond electric pulses," Biochemical and Biophysical Research Communications, 310, pp. 286-295 (2003).

White. et al., "Stimulation of Capactiative Calcium Entry in HL-60 Cells by Nanosecond Pulsed Electric Fields," The Journal of Biological Chemistry, 279(22), pp. 22964-22972 (2004).

Wong et al., "Cell relaxation after electrodeformation: effect of latrunculin A on cytoskeletal actin," Journal of Biomechanics, 38, pp. 529-535 (2005).

\* cited by examiner

Fig. 1A
Fig. 1B
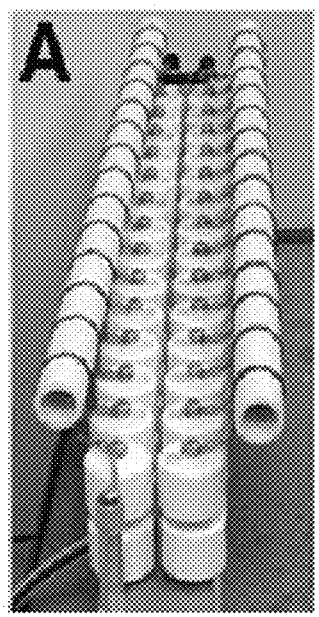
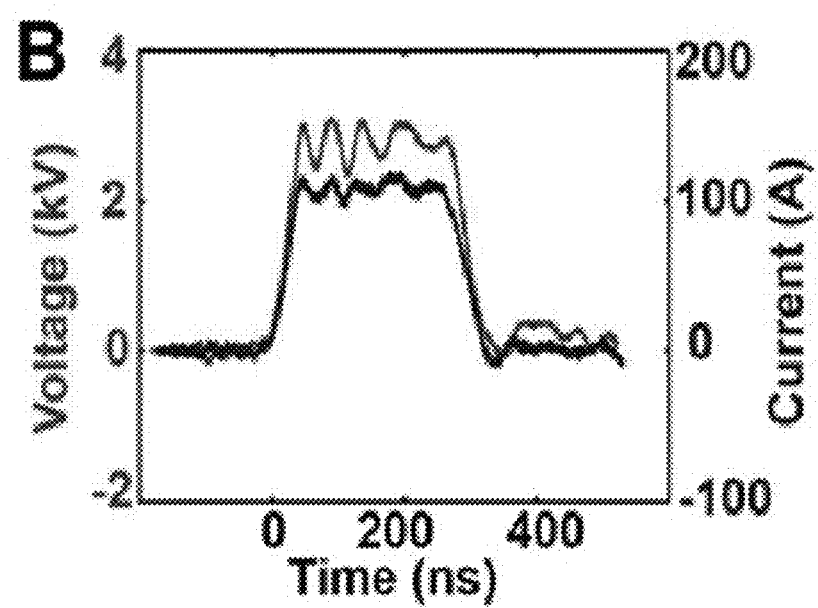
Figures 1A – 1B

Fig. 2A
Fig. 2B
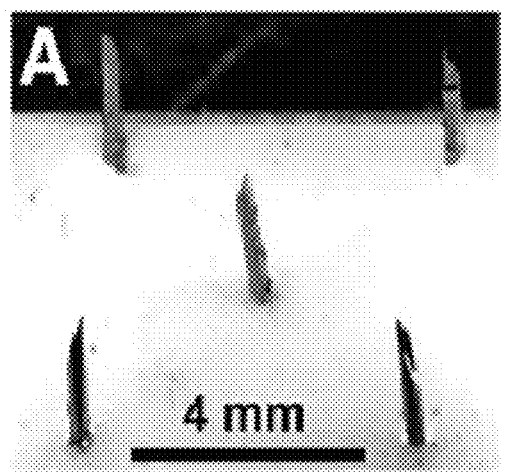
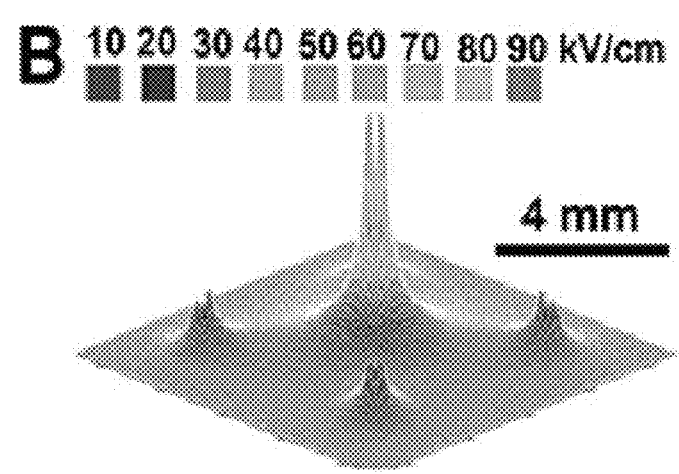
Figures 2A – 2B

Fig. 4A
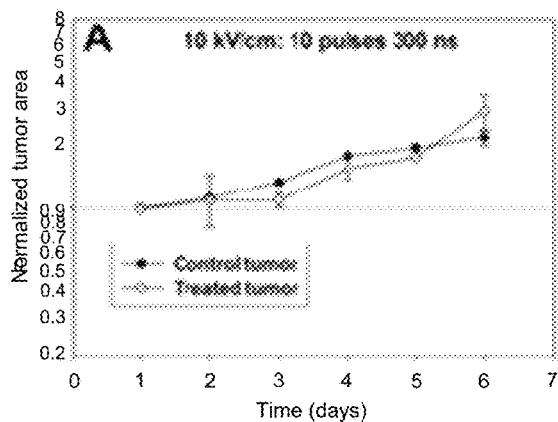
Fig. 4B
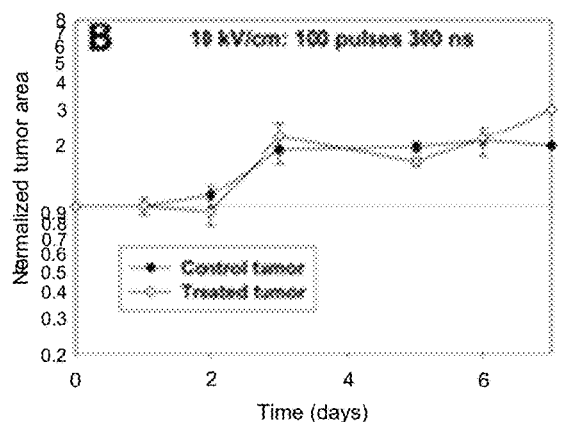
Fig. 4C
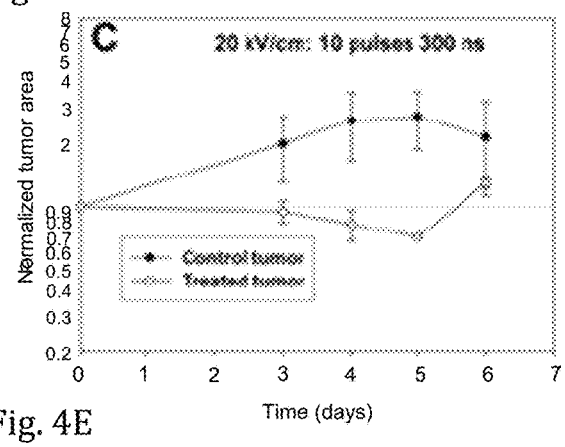
Fig. 4D
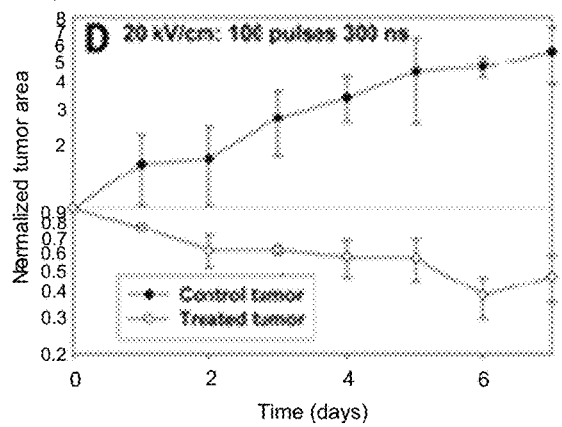
Fig. 4E
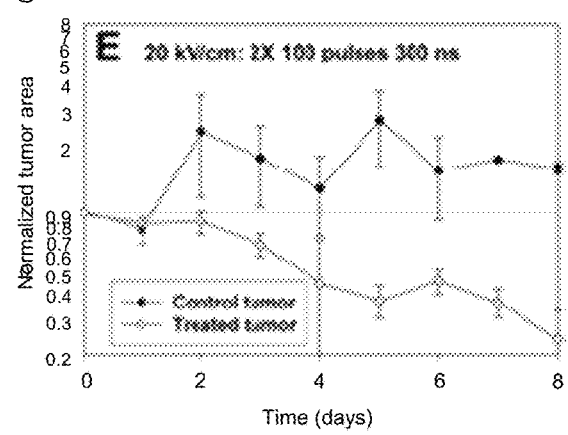
Figures 4A – 4E

Figure 5A-D
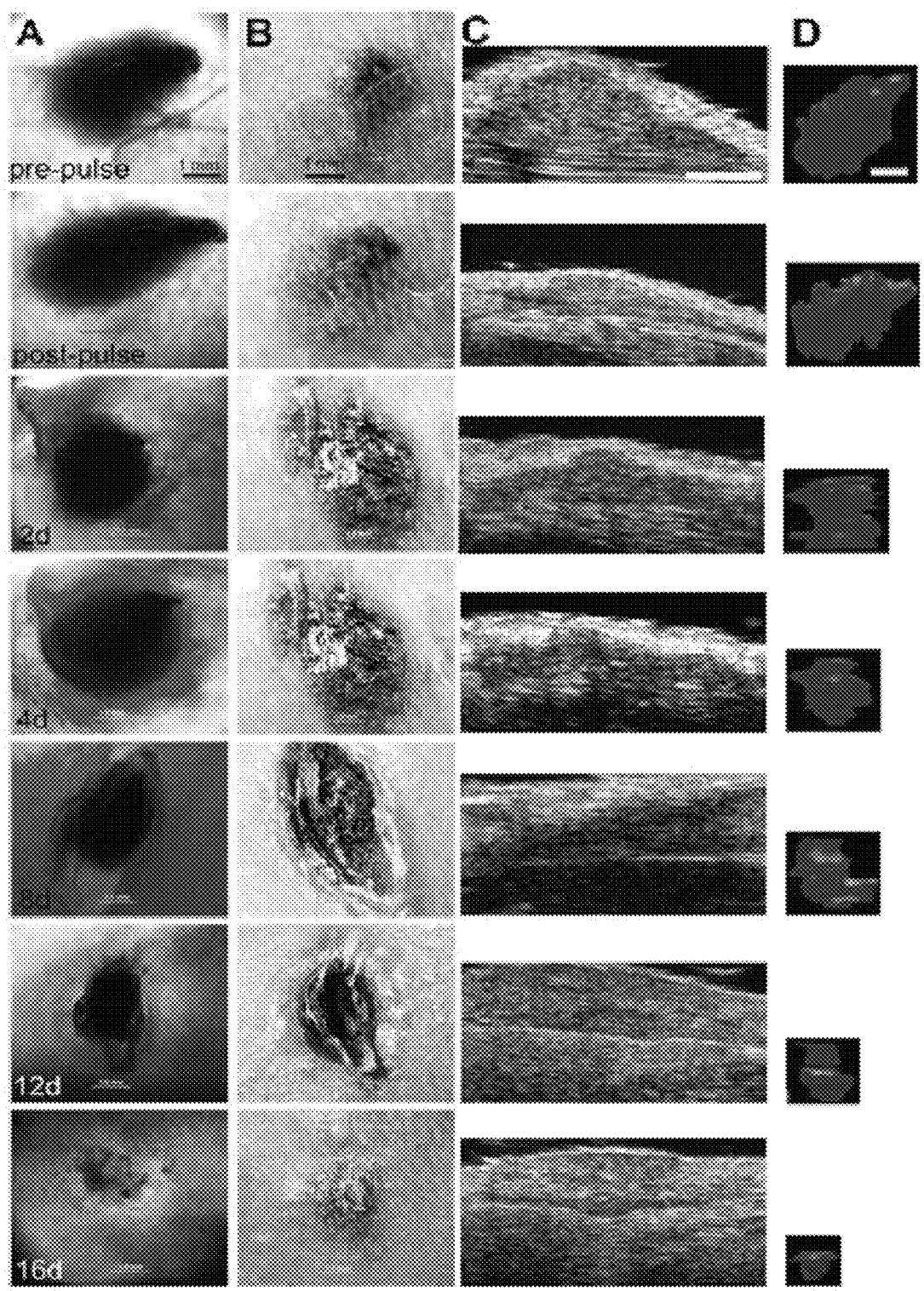

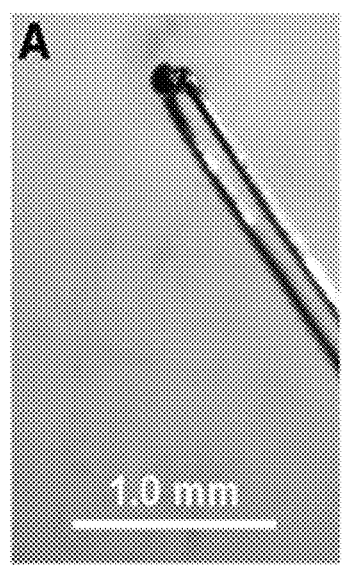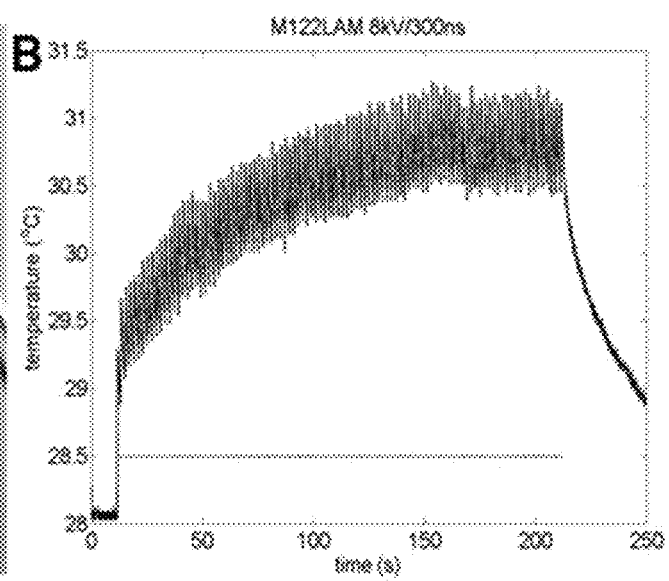
Fig. 8A    Fig. 8B
Figures 8A – 8B

Fig. 9A
Fig. 9B
Fig. 9C
Fig. 9D
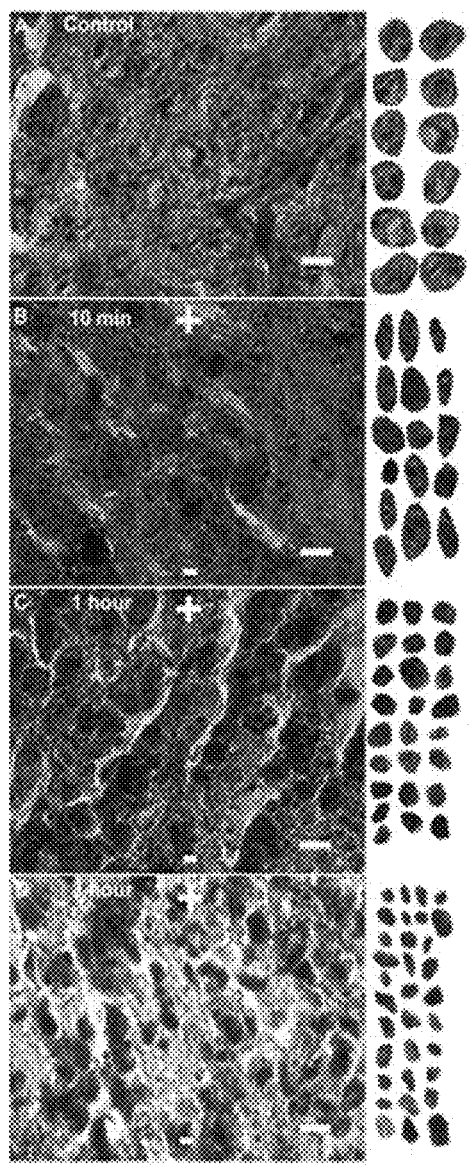
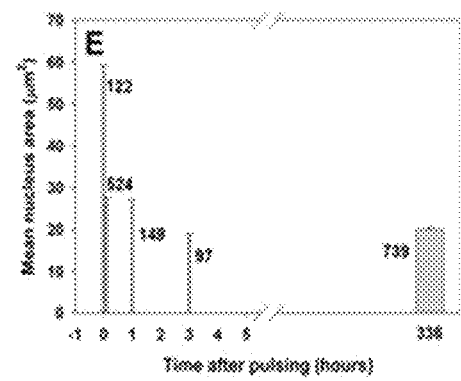
Fig. 9E
Figure 9A – 9E

Fig. 10A
Fig. 10B
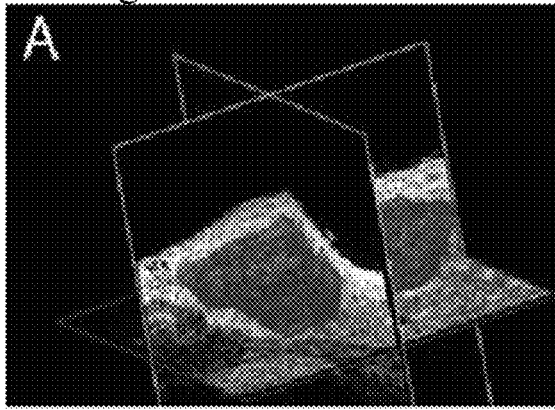
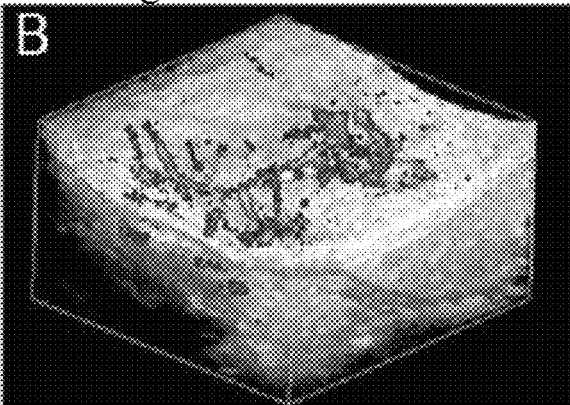
Fig. 10C
Fig. 10D
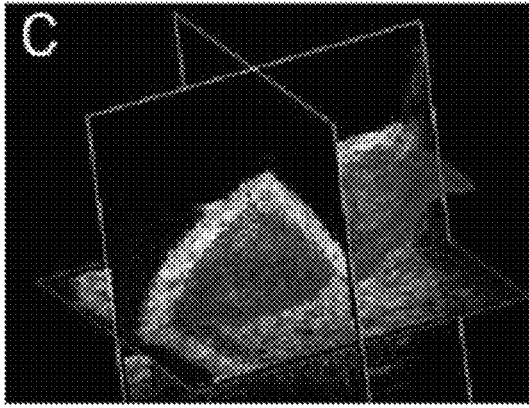
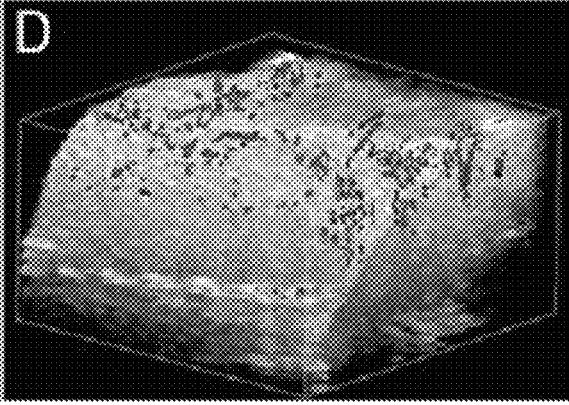
Figures 10A – 10D

NANOSECOND PULSED ELECTRIC FIELDS
CAUSE MELANOMAS TO SELF-DESTRUCT

CROSS-REFERENCE TO RELATED
APPLICATIONS

This application is a continuation of U.S. patent application Ser. No. 14/869,286, filed Sep. 29, 2015, now U.S. Pat. No. 9,943,684, issued Apr. 17, 2018, which is a continuation of U.S. patent application Ser. No. 12/280,280, filed Dec. 21, 2010, now U.S. Pat. No. 9,168,373, issued Oct. 27, 2015, which is a National Stage Entry of International Application No. PCT/US07/04844, filed Feb. 26, 2007, which claims priority to U.S. Provisional Application No. 60/776,215, filed Feb. 24, 2006, the disclosures of which are hereby incorporated by reference in their entireties.

STATEMENT AS TO RIGHTS TO INVENTIONS
MADE UNDER FEDERALLY SPONSORED
RESEARCH AND DEVELOPMENT

The present invention was made with Government support under a grant from the Air Force Office of Scientific Research (AFOSR BioMURI, F49620-02-1-0320). The Government may have certain rights in the invention.

BACKGROUND OF THE INVENTION

Electric fields have been employed in several different types of cancer therapy. Some of these involve radio frequency or microwave devices that heat the tumor to greater than 43° C. to kill the cells via hyperthermia (K. K. Tanabe, S. A. Curley, G. D. Dodd, A. E. Siperstein, S. N. Goldberg (2004) *Cancer.* 100:641-650; D. Haemmerich, P. F. Laeseke (2005) *Int. J. Hyperthermia.* 21:755-760). Others use pulsed electric fields to permeabilize the tumor cells to allow the introduction of toxic drugs or DNA (M. L. Lucas, R. Heller (2003) *DNA Cell Biol.* 22:755-763; Y. Kubota, Y. Tomita, M. Tsukigi, H. Kurachi, T. Motoyama, L. M. Mir (2005) *Melanoma Res.* 15:133-134; A. Gothelf, L. M. Mir, J. Gehl (2003) *Cancer Treat. Rev.* 29:371-387). Previous studies have shown that fibrosarcoma tumors, treated in situ with nanosecond pulsed electric fields, exhibited a reduced growth rate compared to control tumors in the same animal (S. J. Beebe, P. Fox, L. J. Rec, K. Somers, R. H. Stark, K. H. Schoenbach (2002) *IEEE Transactions on Plasma Science.* 30:286-292).

The main characteristics of nanosecond pulsed electric fields (nsPEF) are their low energy that leads to very little heat production and their ability to penetrate into the cell to permeabilize intracellular organelles (K. H. Schoenbach, S. J. Beebe, E. S. Buescher (2001) *Bioelectromagnetics.* 22:440-448; E. S. Buescher, K. H. Schoenbach (2003) *IEEE Transactions on Dielectrics and Electrical Insulation.* 10:788-794) and release calcium (P. T. Vernier, Y. H. Sun, L. Marcu, S. Salemi, C. M. Craft, M. A. Gundersen (2003) *B B R C.* 310:286-295; E. S. Buescher, R. R. Smith, K. H. Schoenbach (2004) *IEEE Transactions on Plasma Science* 32:1563-1572; J. A. White, P. F. Blackmore, K. H. Schoenbach, S. J. Beebe (2004) *J. Biol. Chem.* 279:22964-22972) from the endoplasmic reticulum (J. A. White et al. (2004) *J. Biol. Chem*). They provide a new approach for physically targeting intracellular organelles with many applications, including the initiation of apoptosis in cultured cells (S. J. Beebe, P. M. Fox, L. J. Rec, E. L. Willis, K. H. Schoenbach (2003) *FASEB J.* 17:1493-1495; S. J. Beebe, J. White, P. F. Blackmore, Y. Deng, K. Somers, K. H. Schoenbach (2003) *DNA Cell Biol.* 22:785-796; S. J. Beebe, P. F. Blackmore, J. White, R. P. Joshi, K. H. Schoenbach (2004) *Physiol Meas.* 25:1077-1093) and tumors (S. J. Beebe et al. (2002) *IEEE Transactions on Plasma Science*) enhancement of gene transfection efficiency (S. J. Beebe et al. (2003) *DNA Cell Biol*; S. J. Beebe et al. (2004) *Physiol Meas.*) and reducing tumor growth (S. J. Beebe et al. (2002) *IEEE Transactions on Plasma Science*).

The use of electric fields on biological cells to rupture the cell membrane can lead to cell death via necrosis, a non-physiological type of cell destruction, while the use of nsPEFs on biological cells to permeabilize intracellular organelles can initiate cell death via apoptosis. When treating biological cells within tissue in situ, being able to initiate cell death via apoptosis would allow the destruction of specific undesired cells in situ without engendering the non-specific damage to surrounding or nearby tissue in the body due to inflammation and scarring that is normally observed with necrosis. Investigations of the effects of ultrashort, high intensity pulsed electric fields or nanosecond pulsed electric fields (nsPEF) on mammalian cells have demonstrated distinct differences on cell structure and function compared to classical plasma membrane electroporation. It was previously demonstrated that nsPEF invoked signal transduction mechanisms that initiate apoptosis cascades in several human cell lines including HL-60 cells (Beebe, S. J., et al. (2002) *IEEE Trans. Plasma Sci.* 30, 286-292; Beebe, S. J., et al. (2003) *FASEB J.* 17, 1493-1495).

The efficacy of this nsPEF treatment is believed to depend on two separate electric field parameters: pulse duration and amplitude. The effect of pulse duration can be understood by considering the process of membrane charging when the cell is placed in an electric field. Ions in the cell interior will respond to the electric field by moving in the field direction and charging the highly resistive membrane until they experience no further force. By definition this will only occur when their redistribution establishes an equal and opposite field so that the net electric field in the cell interior is zero. However this redistribution takes a certain amount of time that is characterized by the charging time constant of the plasma membrane, typically in the 0.1 to 1 microsecond range. If the nsPEF is shorter than this charging time, the interior charges will not have sufficient time to redistribute to counteract the imposed field and it will penetrate into the cell and charge every organelle membrane for a duration which is dependent on both the charging time constant of the cell's plasma membrane as well as that of the organelle membrane (K. H. Schoenbach, R. P. Joshi, J. F. Kolb, N. Chen, M. Stacey, P. F. Blackmore, E. S. Buescher, S. J. Beebe (2004) *Proc. IEEE.* 92:1122-1137).

A second critical nsPEF parameter is the amplitude of the pulse. Both the force exerted on charges and the electroporation of lipid membranes depend on the strength of the electric field. When the electric field across a cellular membrane exceeds about 1 volt (2 kV/cm for a cell 10 µm in diameter), water-filled pores form in the membrane's lipid bilayer and the size and lifetime of these pores are dependent on the strength and duration of the electric field pulse. For amplitudes exceeding 2 kV/cm and pulse durations in the millisecond range, large pores form resulting in electroporation of the membrane that has been used to introduce normally impermeant anticancer drugs into targeted tissues (M. L. Lucas et al (2003) *DNA Cell Biol.*; Y. Kubota et al (2005) *Melanoma Res.*; A. Gothelf et al (2003) *Cancer Treat. Rev.*; J. Teissie, M. Golzio, M. P. Rols (2005) *Biochim. Biophys. Acta* 1724:270-280). For these long pulses, the pulse amplitude is limited to about 2 kV/cm to avoid thermal effects. Since heating is proportional to pulse duration and the square of the field strength, the much shorter pulses in the nanosecond range can have a higher field strength while delivering the same low level of thermal energy to the tissue. A 20-fold higher field strength of 40 kV/cm can be employed to generate structural changes in the plasma membrane that result in a smaller electrical barrier as well as higher voltage gradients across cellular organelles for the duration of the pulse (Q. Hu, S. Viswanadham, R. P. Joshi, K. H. Schoenbach, S. J. Beebe, P. F. Blackmore (2005) *Phys. Rev. E Stat. Nonlin. Soft. Matter Phys.* 71:031914-1-031914-9). A typical tumor cell nucleus measuring 10 µm in diameter will experience a voltage gradient of roughly 40 V across its diameter during each pulse. This electric field is large enough to cause electrodeformation (R. P. Joshi, Q. Hu, K. H. Schoenbach, H. P. Hjalmarson (2002) *Phys. Rev. E Stat. Nonlin. Soft. Matter Phys.* 65:021913).

Previous studies provided direct evidence for cellular DNA as a direct or indirect target of nsPEF. Using a comet assay, Stacey, et al. (M. Stacey, J. Stickley, P. Fox, V. Statler, K. Schoenbach, S. J. Beebe, S. Buescher (2003) *Mutat. Res.* 542:65-75) found that ten 60 ns pulses of 60 kV/cm caused a rapid 2.6-fold increase in the mean image length of DNA electrophoresis tracks in Jurkat cell extracts and a 1.6-fold increase in the comet assay from HL60 cell extracts. In both cases this was a very significant change (p<0.001). This elongation in DNA electrophoresis tracks is normally interpreted to indicate fragmentation of the DNA into smaller pieces that is associated with apoptotic cell death. An indication of changes in the DNA following nsPEF treatment comes from images of the nucleus labeled with acridine orange, a vital fluorescent dye that intercalates into DNA and RNA, Chen et al. (N. Chen, K. H. Schoenbach, J. F. Kolb, S. R. James, A. L. Garner, J. Yang, R. P. Joshi, S. J. Beebe (2004) *Biochem. Biophys. Res. Commun.* 317:421-427). A single 10 ns pulse of 26 kV/cm caused a dramatic decrease in fluorescence intensity in the nucleus evident as early as 5 min after the pulse. This change could be due to an outflow of DNA or to conformational changes in the DNA.

The ability to selectively modify specific cells in ways that lead to apoptosis could provide a new method for the selective destruction of undesired tissue (e.g., cancer cells, fat cells or cartilage cells) while minimizing side effects on surrounding tissue. An electrical method of treatment that results, not only in tumor growth inhibition, but in complete tumor regression, without hyperthermia, drugs, or significant side effects, would be a great advancement in the field of cancer therapy and other in situ therapies. These and various other needs are addressed, at least in part, by one or more embodiments of the present invention.

BRIEF SUMMARY OF THE INVENTION

One or more aspects of the invention provide a method for selectively initiating apoptosis in target cells in a tissue. The method comprises applying at least one nsPEF to said tissue. The at least one nsPEF has a pulse duration of at least about 10 nanoseconds and no more than about 1 microsecond and an electric field pulse strength of at least about 10 kV/cm and no more than about 350 kV/cm. In one or more embodiments of the invention, the method is carried out in situ.

In one aspect, at least one nsPEF has a pulse duration of about 300 nanoseconds and an electric field pulse strength of at least about 20 kV/cm and no more than about 40 kV/cm.

In one or more embodiments of the invention, at least 100 nsPEFs are applied to said tissue. In one aspect, at least 300 nsPEFs are applied to the tissue. In another aspect, at least 400 nsPEFS are applied to the tissue. In yet another embodiment of the invention, the method of treatment of at least one nsPEF is repeated.

In one or more aspects of the invention, the target cells are fat cells. In one or more aspects of the invention, the target cells are bone cells. In one or more aspects of the invention, the target cells are vascular cells. In one or more aspects of the invention, the target cells are muscle cells. In one or more aspects of the invention, the target cells are cartilage cells. In one or more aspects of the invention, the target cells are stem cells. In one or more aspects of the invention, the target cells are a combination of the above cells.

Also provided in the invention is a method for inhibiting blood flow in a tissue. The method comprises applying at least one nsPEF to said tissue. The at least one nsPEF has a pulse duration of at least about 10 nanoseconds and no more than about 1 microsecond and an electric field pulse strength of at least about 10 kV/cm and no more than about 350 kV/cm. In one or more embodiments of the invention, the method is carried out in situ.

The invention also provides a method for inducing tumor regression. The method comprises applying at least one nsPEF to said tumor. The at least one nsPEF has a pulse duration of at least about 10 nanoseconds and no more than about 1 microsecond and an electric field pulse strength of at least about 10 kV/cm and no more than about 350 kV/cm. In one or more embodiments of the invention, the method is carried out in situ.

BRIEF DESCRIPTION OF THE FIGURES

FIGS. 1A-1B depicts the pulse generator used in these experiments. (A) 300 ns pulse-forming network in Blumlein configuration. (B) Typical voltage and current pulse generated across a tumor.

FIGS. 2A-2B depicts the needle array electrode and electric field pattern. (A) Photograph of 5 needle array used for the first experiments. (B) 3-D plot of the electric field generated when 8 kV is placed on the center electrode and the outer four electrodes are held at ground.

FIGS. 4A-4E provide a summary of the size changes in a total of 23 melanomas after the indicated treatments using the 5-needle array. For each day the tumor area was measured from the transillumination image and divided by that measured on day zero to give the normalized area. The average response of two to three tumors from different animals is plotted on a logarithmic scale and the error bars represent the S.E.M. Pulses were applied at a frequency of 0.5 Hz. (A-B) 4 kV was applied between center and outer needles spaced 4 mm apart to give an average field of 10 kV/cm. C-E: 8 kV was applied between the center and outer needles to give an average field of 20 kV/cm.

FIG. 5A-D depicts a typical response of a melanoma to three applications of 100 pulses (300 ns, 40 kV/cm, 0.5 Hz) 30 minutes apart on day 0 followed by a single application on day 4 using a 5 mm diameter parallel plate electrode on mouse #102. Collection of 7 matched sets of images of the same tumor all taken on the day indicated in the lower left corner of the transillumination image. Column A: Transillumination image. Column B: Surface view. Column C: Ultrasound slice at center of tumor; Column D: 3-D reconstruction made from 100 serial ultrasound slices through tumor. Magnification is constant for each column and scale bar at top of each column represents 1 mm.

Figure 6A:
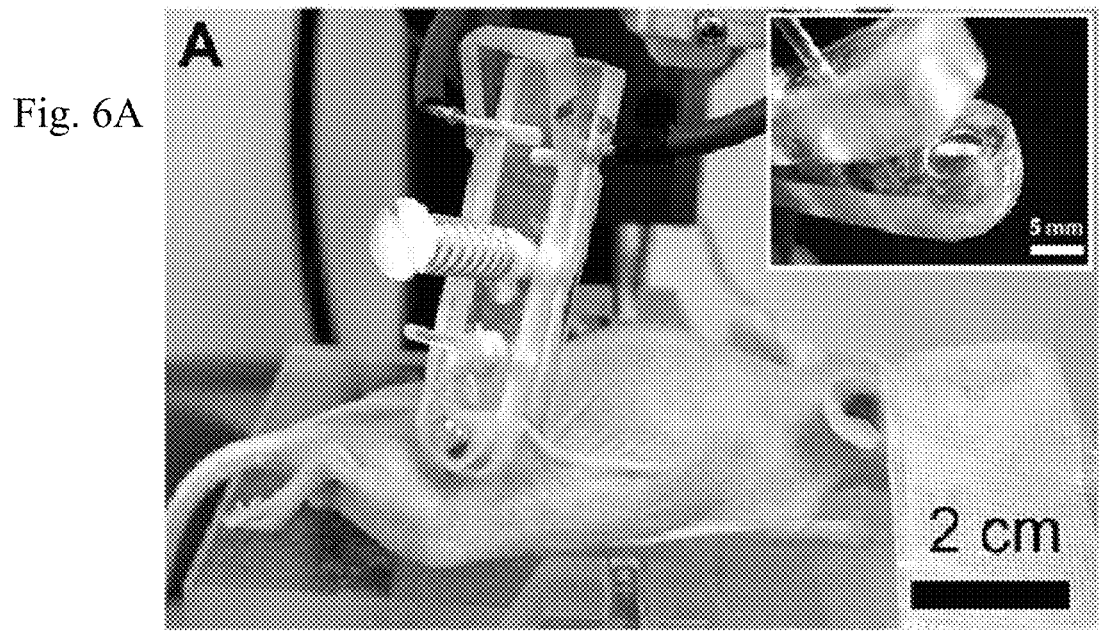
Figure 6B:
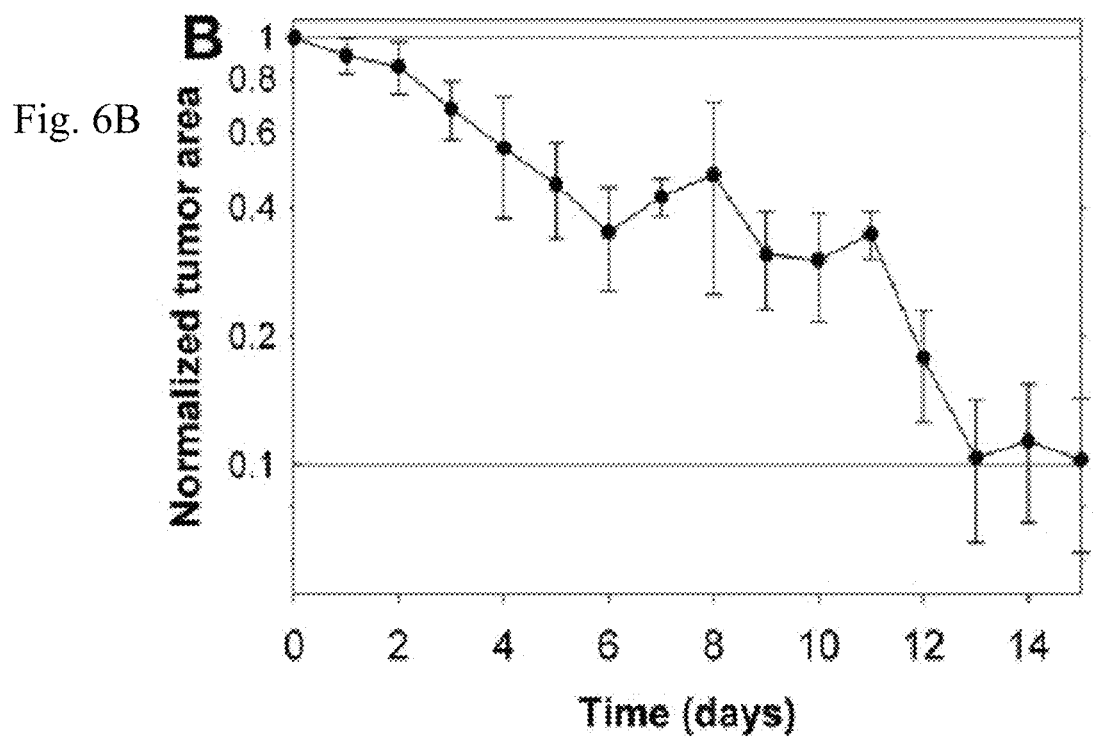

FIG. 6A shows a photograph of SKH-1 hairless mouse being treated with parallel plate electrode under isoflurane inhalation anesthesia. Inset: Close-up of one of the plates of parallel plate electrode showing it recessed by 0.5 mm to allow a space for a conductive agar gel to be placed on it. FIG. 6B shows Mean change in normalized area of the transillumination image of 6 tumors from 3 mice treated with parallel plate electrodes using the same 4×100 pulse applications (3×100 on day 0 and 1×100 on day 4). 40-80 kV/cm, 300 ns pulses at 0.5 Hz. Error bars indicate the S.E.M.

Figure 7:
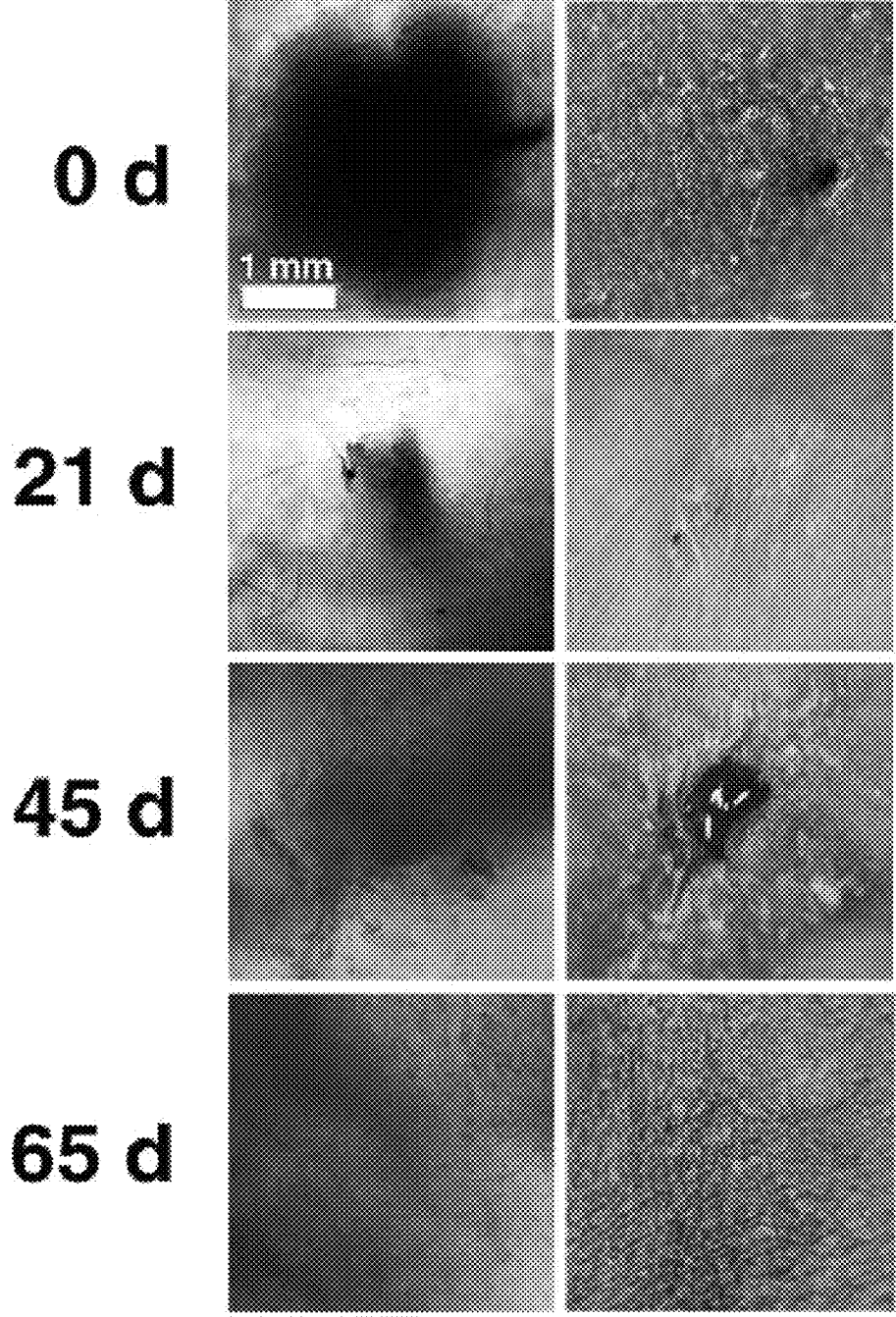

FIG. 7 shows complete regression of melanoma evident by 65 days after the first treatment. 100 pulses of 300 ns and 40 kV/cm were applied on days 0, 1, 2 and 21, 22, 23. Each pair of photos were taken on the day indicated at the left; transillumination on left and surface view on right. The scale bar in upper left represents 1 mm and is the same for all images.

FIGS. 8A-8B depict the measurement of the temperature within a melanoma during nsPEF application. (A) Micrograph of a thermocouple made by fusing a copper wire with one made from constantine. (B) Temperature record from a thermocouple positioned inside of a melanoma during pulse application. Red dots indicate the time that each pulse was applied.

FIGS. 9A-9E depict targets and mechanisms of nsPEF effects. (A-D) 7 µm thick paraffin sections of control and treated melanomas fixed at the indicated time after treatment with 100 pulses (300 ns, 40 kV/cm, 0.5 Hz) stained with hematoxylin and eosin. The clearest nuclei were copied and placed to the right of each section to assist in size comparison. (A) Control tumor section; (B) 10 min post treatment (C) 1 h post treatment. (D) 3 h post treatment. Scale bars: 10 µm. (E) Mean nuclear area versus time after 100-200 pulses were applied. Number of cell nuclei measured from at least two mice for each time point indicated next to each column and bars represent S.E.M. Break in time is 330 hours. There is a significant difference between the 0 hr prepulse control and all of the other time points (p<0.001) as well as between 1 and 3 hours (p<0.001). There is no significant difference between 0.1 and 1 hour.

FIGS. 10A-10D show the blood flow in melanoma before and after nsPEF application. (A) 3-D reconstruction of volume of melanoma; (B) Power Doppler reconstruction of blood flow before field application. (C) 3-D reconstruction of volume of same melanoma shown in A generated about 15 minutes after 100 pulses (300 ns, 40 kV/cm, 0.5 Hz). (D) Power Doppler reconstruction of blood flow in the same tumor shown in B generated about 15 minutes after 100 pulses (300 ns, 40 kV/cm, 0.5 Hz)

Figure 11:
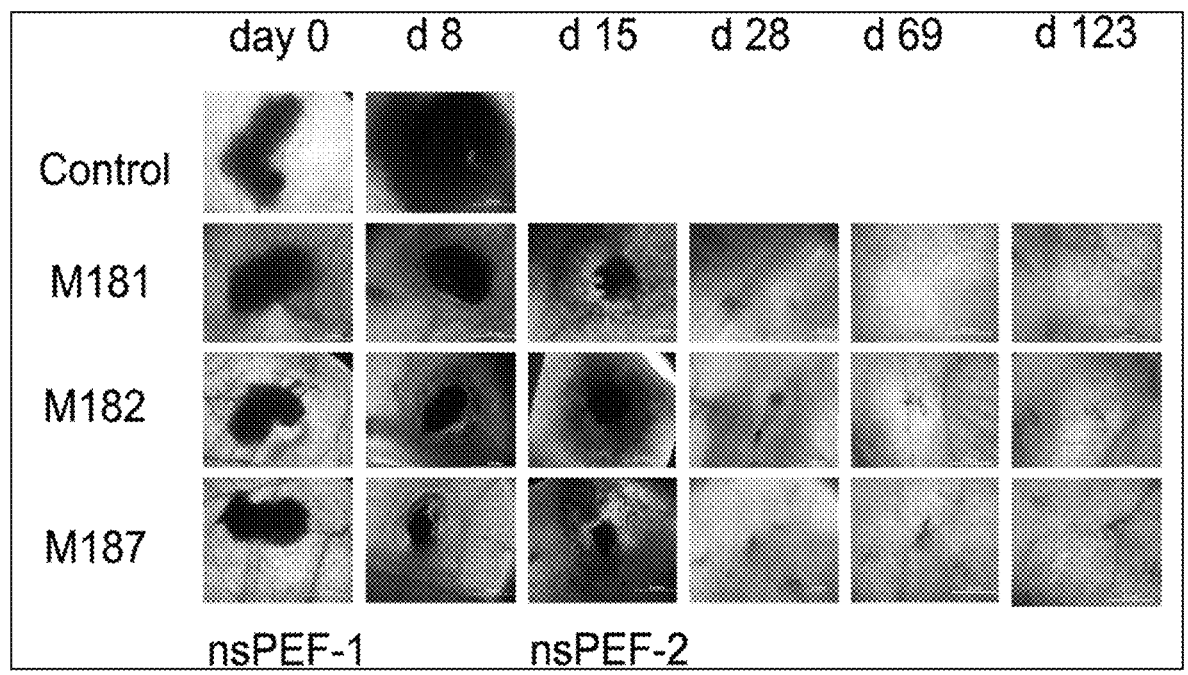

FIG. 11 shows transillumination views of one control and three treated tumors at the day indicated at the top of each column. Photo in day 0 was taken just before the first nsPEF application. A second application of 300 pulses occurred on day 15. No other treatments were needed and these animals remain tumor-free to date.

Figure 12:
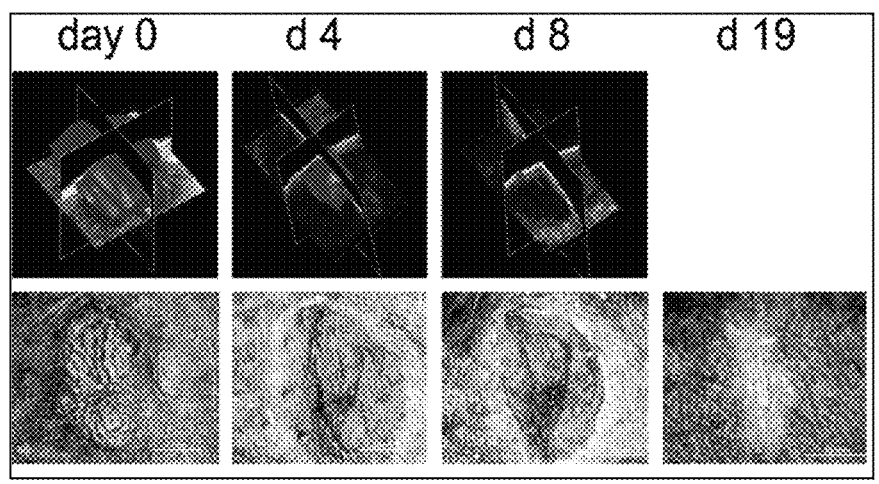

FIG. 12 shows a UV-induced melanoma in a HGF/SF transgenic mouse that was treated on day 0 with 300 pulses 300 ns long and 40 kV/cm in amplitude. 3D reconstruction of serial section; ultrasound images (top row) and surface micrographs (bottom row) indicate that the tumor shrinks rapidly over the 19-day period studied to date.

Figure 13:
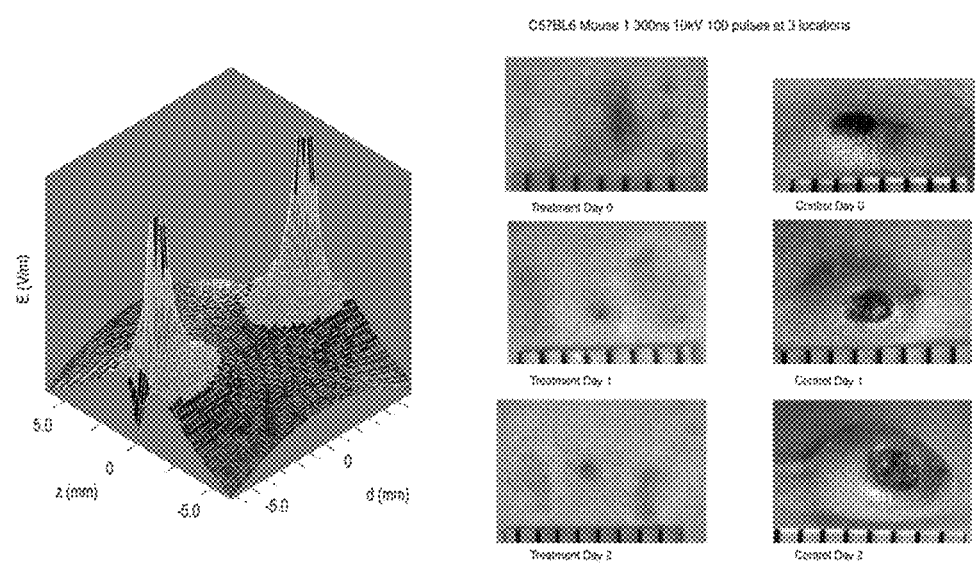

FIG. 13 shows the computed electrical field distribution (in arbitrary units for a two-needle electrode configuration system in a linear array). The series of photographs on the right shows the temporal development of the tumor.

DETAILED DESCRIPTION OF THE INVENTION

For the purposes of promoting an understanding of the principles of the invention, reference will now be made to preferred embodiments and specific language will be used to describe the same. It will nevertheless be understood that no limitation of the scope of the invention is thereby intended. Rather, such alterations and further modifications of the invention, and such further applications of the principles of the invention as illustrated herein, as would be contemplated by one having skill in the art to which the invention relates are intended to be part of the present invention.

For example, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

Biological cells consist of cytoplasm surrounded by a membrane. The cytoplasm is conducting, while the membrane, which is made up of a lipid bilayer, can be considered a dielectric. The application of electric fields to biological cells causes buildup of electrical charge at the cell membrane, and consequently a change in voltage across the membrane. For eukaryotic cells the transmembrane voltage under equilibrium condition is approximately 70 mV. In order to affect membrane processes by means of external electric fields, the amplitude of these electric fields ("E") must be such that it generates a potential difference ("$V_m$") at least on the same order as the resting potential. The amplitude of the electric field is:

$$E = V_m/fa \quad (1)$$

where a is the radius of the cell and f is a form factor which depends on the shape of the cell. For spherical cells, f is 1.5; for cylindrical cells of length 1, with hemispheres of diameter d at each end, the form factor is $$f = 1/(1-d/3) \quad (2)$$

For a biological cell with an assumed radius of about 5 µm and a spherical shape, the external electric field required to generate a voltage of the same amplitude as the resting potential across the membrane is on the order of 100 V/cm.

For external electric fields of a magnitude such that the change in membrane potential is on the order of the resting potential, voltage induced opening of channels in the membrane causes flux of ions through the membrane. This leads to changes in the ion concentration close to the cell membrane, and consequently causes cell stress. The stress lasts on the order of milliseconds, and generally does not cause permanent cell damage. If the strength of the electric field is increased such that the voltage across the cell membrane reaches levels on the order of one volt, the membrane permeability increases to such a level that either the cell needs from seconds to hours to recover (reversible breakdown), or cell death may occur. The mechanism of the membrane breakdown is not well understood. A common hypothesis is that pores are generated in the membrane. The pores can be of sizes that allow the exchange of macromolecules. If the transmembrane voltages are sufficiently high the pores will not close anymore. The use of the reversible breakdown effect has been reported in electroporation and in biofouling prevention. The irreversible effect has been employed in the debacterialization of water and food.

The effect of electric fields on biological cells is not simply dependent on the magnitude of the applied electric field, but also on its duration. When a voltage pulse is applied to the cell, charges accumulate at the membrane and the membrane voltage is increased.

An "nsPEF" or "nanosecond pulsed electric field" as used herein is defined as an electric pulse in the nanosecond range (about 100 picoseconds to about 1 microsecond) with electric field intensities from about 10 kV/cm to about 350 kV/cm. For delivery of nsPEFs to cells, any apparatus equipped with a pulse generator that can deliver short electrical pulses of pulse duration of at least about 100 picoseconds and no more than about 1 microsecond, and of electric field strength of at least about 10 kV/cm and no more than about 350 kV/cm, may be used. In another aspect of the invention, the pulse generator can deliver short electrical pulses of pulse duration of at least about 100 picoseconds and no more than about 1 microsecond, and of electric field strength of at least about 10 kV/cm and no more than about 40 kV/cm. In another aspect of the invention, the pulse generator can deliver short electrical pulses of pulse duration of at least about 100 picoseconds and no more than about 1 microsecond, and of electric field strength of at least about 20 kV/cm and no more than about 125 kV/cm. In another aspect of the invention, the pulse generator can deliver short electrical pulses of pulse duration of at least about 10 nanoseconds and no more than about 300 nanoseconds, and of electric field strength of at least about 20 kV/cm and no more than about 45 kV/cm. In another aspect of the invention, the pulse generator can deliver short electrical pulses of pulse duration of at least about 10 nanoseconds and no more than about 350 nanoseconds, and of electric field strength of at least about 20 kV/cm and no more than about 125 kV/cm. In another aspect of the invention, the pulse generator can deliver short electrical pulses of pulse duration of about 10 nanoseconds and an electric field strength of about 125 kV/cm. In another aspect of the invention, the pulse generator can deliver short electrical pulses of pulse duration of about 300 nanoseconds and an electric field strength of about 40 kV/cm.

The apparatus for delivery of nsPEFs is also equipped with a high voltage power supply and with a means for directing the nsPEFs to the target cells. Preferably, the target cells are in situ, and any suitable means for directing the nsPEFs to the in situ target cells may be employed. Suitable means for directing the nsPEFs will preferably allow high voltage, short duration electrical pulses in the nanosecond range, for example, within tissues. Examples include an electrode system, such as plate electrodes, needles or needle arrays. In one or more embodiments of the invention, the nsPEFs are applied directly to cells present as part of a tissue.

The nsPEF pulses of the present invention can be administered to the cells by means of a pulse generator, such as the generator previously described in U.S. Pat. No. 6,326,177 and Beebe et al. *FASEB J.* 17, 1493-1495 (2003). Prior to the above-described pulse generator, the application of these high frequency intracellular effects had been limited due to the difficulty of generating large intracellular electric fields on a time scale that is comparable to or even less than the charging time of the surface. However, as described in U.S. Pat. No. 6,326,177 and Beebe et al. (2003), the present inventors developed technology for generating high voltage, short duration electrical pulses that make it possible to produce electric pulses in the nanosecond range with voltage amplitudes adequate to generate electric fields near MV/cm in suspensions of cells or within tissues (Mankowski, J., Kristiansen, M. (2000) *IEEE Trans Plasma Science* 28:102-108). Because of their nanosecond duration, the average energy transferred to the cells/tissues by these pulses is theoretically negligible, resulting in electrical effects without accompanying thermal effects.

The electric field strength (or electric field intensity) of the nsPEF pulse to be applied to cells is the applied voltage divided by the distance between the electrodes, and is generally at least about 10 kV/cm, but should not exceed the breakdown field of the suspension or tissue which includes the cells. The breakdown field increases with decreasing pulse duration, and can be experimentally determined. Under the conditions commonly employed in the present invention, however, the breakdown field generally does not exceed 500 kV/cm. In one or more aspects of the invention, electric field pulses that have durations of about 300 nanoseconds and typically have electric field strengths greater than 20 kV/cm with rise times of 30 nanoseconds.

The pulses should preferably be less than one microsecond, but more than about 100 picoseconds in duration. In one or more aspects of the invention, a pulse duration is about 1 nanosecond to about 300 nanoseconds. The optimum pulse duration will vary depending on the cell type, tissue type, and desired treatment, among other factors.

The number of nsPEF pulses, and the number of any successive treatments to be applied to the tissue, is that sufficient to induce complete regression of the undesired tissue, for example, complete tumor regression. This number may vary based on a variety of factors included the intended effect, the mode of administration of the nsPEFs, and the cells to be treated.

Notably, the nsPEFs are distinct from electroporation pulses based on their temporal and electrical characteristics, as well as their effects on intact cells and tissues. For comparative purposes, electroporation pulses and nsPEFs, respectively, exhibit different electric field strength (1-5 kV/cm vs. 10-350 kV/cm); different pulse durations (0.1-20 milliseconds vs. 1-300 nanoseconds); different energy densities (joules/cc vs. millijoules/cc) and different power (500 W vs. 180 MW). Thus, nsPEFs can be five to six orders of magnitude shorter with electric fields and power several orders of magnitude higher and energy densities considerably lower than electroporation pulses. In addition to the unique short duration and rapid rise time, nsPEFs are exceptional because they are very low energy and extremely high power. Stemming from these differences, as the pulse duration decreases, nsPEFs bypass the plasma membrane and target intracellular structures such as the mitochondria, endoplasmic reticulum, Golgi apparatus, nucleus, or any intracellular store, leaving the plasma membrane intact. These pulses have effects that are unexpectedly different than those of electroporation pulses because, when the pulse duration is short enough and the electric field intensity is high enough, intracellular structures are targeted. The effects of nsPEFs on cells differ depending on the cell type, pulse duration and rise-time, electric field intensity, and/or other factors.

In addition, nsPEFs and electroporation pulses have different effects on cells. For example, Jurkat cells exposed to classical electroporation pulses (e.g. 100 μs) exhibited immediate propidium iodide ("PI") uptake, but when exposed to 60 or 300 ns they took up PI at much later times, consistent with apoptosis induction (Deng, J., et al. (2003), *Biophys. J.* 84, 2709-2714). Furthermore, in contrast to classical electroporation effects where larger cells are more readily electroporated than smaller cells, nsPEFs have greater plasma membrane effects on smaller cells (e.g. T-cells) than larger ones (e.g. monocytes). Under conditions that are independent of plasma membrane electroporation, nsPEFs have been shown to alter signal transduction mechanisms that determine cell fate. Using nsPEFs, it is possible to trigger apoptosis (Beebe, S. J., et al. (2002), *IEEE Trans. Plasma Sci.* 30:1 Part 2, 286-292; Beebe, S. J., et al. (2003), *FASEB J* (online, Jun. 17, 2003) 10.1096//fj.02-0859fje; Vernier, P. T., et al. (2003), *Biochem. Biophys. Res. Comm.* 310, 286-295). nsPEFs induced several well-characterized apoptosis markers including intact plasma membranes, annexin-V-FITC binding, caspase activation, cell shrinkage, cytochrome c release into the cytoplasm, and ultimately, a late secondary necrosis as defined by rupture of the plasma membrane in vitro in the absence of phagocytosis (Beebe et al., 2003).

One or more embodiments of the invention are directed to a method of treating melanomas with a second, or multiple, treatments to lead to complete tumor remission.

Other embodiments of the invention involve the use of nsPEFs in patients to cause tumor blood flow to stop. In another embodiment, the use of nsPEFs in patients cause the inhibition of blood flow to any particular tissue.

Reference will now be made to specific examples illustrating the use of nsPEFs in inducing complete tumor regression. It is to be understood that the examples are provided to illustrate preferred embodiments and that no limitation of the scope of the invention is intended thereby.

Example 1: Applying nsPEFs to Treat Melanomas

Materials and Methods

Cell Tissue Culture—

Murine melanoma B16-F10 cells were obtained from ATCC (Manassas, Va.) and were stored frozen in liquid nitrogen until needed. They were thawed in a 37° C. water bath and then transferred to a culture flask containing DMEM (Dulbecco's Modified Eagles Medium) supplemented with 10% fetal bovine serum (FBS, Atlanta Biologicals), 4 mM L-Glutamine (Cellgro), and 2% Penicillin-Streptomycin solution (Cellgro). The cells were grown in a 5% $CO_2$/95% air/100% humidified incubator at 37° C.

Melanoma Induction—

Two to four tumors were induced in 120 female SKH-1 mice (immunocompetent, hairless, albino strain, Charles River, Wilmington, Mass.) by injecting 2-10 μl containing $10^6$ B16-F10 murine melanoma cells just under the skin in the loose areolar tissue. A melanoma tumor can be seen at the injection site within a few days. Within 5 days the tumor is typically 3 mm wide and has exhibited angiogenesis. Untreated tumors typically grow to 10 mm wide or more within a few weeks. For all animal studies the mice were kept under inhalation anesthesia using 1.6% isoflurane in oxygen. Tumors in animals #4-#63 were treated with a 5-needle electrode array and #64-#120 were treated with parallel plate electrodes. In a typical experiment two tumors were used as controls and two others on the same mouse were treated with nsPEF In Vivo Imaging—

Melanomas were imaged daily by both transillumination and surface photography at 1.2× magnification and ultrasound images were also taken beginning with mouse 50. Visualsonics Vevo 770 (Visualsonics Inc., Toronto, Canada) was used to image tumors in situ. The 708 model scan head at 55 MHz with a stepper motor scanner providing a spatial resolution of 30 μm was used (Visualsonics Inc., Toronto, Canada). The power Doppler mode provided blood flow images for each tumor.

Histology—

Phosphate-buffered formalin (10%) was injected into the loose areolar layer under the skin at the tumor site immediately after euthanizing the mouse and 15 min prior to tumor dissection. The tumor was placed in formalin fixative (minimum 20× tumor volume) for 24 to 48 h at room temperature. The tumor and surrounding skin were trimmed and both external and internal surfaces were photographed. The fixed tumor was dehydrated through a standard 30%, 50%, 70%, 80%, 90%, 95%, 100%×3 ethanol series, cleared in 100%×2 xylene, infiltrated at 60° C. in molten paraffin baths×2 (all for 1 h each) and then embedded in paraffin block. Seven μm thick sections were cut and stained with hematoxylin and eosin.

Pulse Generator—

A pulse-forming network with an impedance of 75Ω was used. As shown in FIG. 1A, it consists of 30 pairs of high voltage capacitors and 30 inductors arranged in a Blumlein configuration, and generates a 300 ns long high voltage pulse (J. F. Kolb, S. Kono, K. H. Schoenbach (2006) *Bioelectromagnetics.* 27(3):172-87). The pulse was originally triggered by means of a spark gap that was later replaced by a mercury displacement relay controlled by a microcontroller. In FIG. 1B, voltage across the object was monitored using a high voltage probe (P6015A, Tektronix, Beaverton, Calif.), and the current was measured by means of a Pearson coil (model 2877, Pearson Electronics Inc., Palo Alto, Calif.). Current and voltage were recorded simultaneously using a digitizing oscilloscope (TDS3052, Tektronix, Beaverton, Oreg.).

Electrodes for Electric Field Application—

Three types of electrodes were employed; a 5-needle array, a 2-needle array and parallel plates. The 5-needle array (FIG. 2) was made using 30 gauge hypodermic needles (300 μm diameter) extending 2 mm from a Teflon base. The center needle was the anode and the four surrounding needles spaced 4 mm from the center electrode were connected together forming the cathode. The skin was coated with vegetable oil prior to needle insertion to increase the breakdown field strength along the skin and reduce the likelihood of flashover between needles during the pulsed field application. The parallel plate electrodes (FIG. 6A) were made from stainless steel with diameters of 3-5 mm, depending on the size of the tumor being treated. These electrodes were coated with a 0.5 mm thick layer of conductive agar (1M NaCl in 2% agar) to separate the skin from the electrode. For treatment, each tumor was positioned between two plates with a separation of 0.5-1 mm, while 100 pulses 300 ns in duration and 4-8 kV in amplitude with a rise time of about 30 nanoseconds, were applied at a frequency of 0.5 Hz.

Determination of Caspase Activation In Vitro—

Caspase activity was determined in vitro from melanoma tumor extracts after exposure to nsPEF. Melanomas were dissected out of the mouse and frozen in liquid nitrogen. Extracts were prepared from thawed tissue homogenates and assayed for caspase activity using the fluorogenic substrate Ac-DEVD-AFC (Alexis Biochemicals, San Diego, Calif.) as previously described (L. K. Parvathenani, E. S. Buescher, E. Chacon-Cruz, S. J. Beebe (1998) *J. Biol. Chem.* 273:6736-6743). This peptide sequence is based on the PARP cleavage site, Asp216, for caspases 1, 3, 4 and 7 that exhibits enhanced fluorescence upon cleavage. Briefly, extracts were incubated with 50 µM DEVD-AFC (Asp-Glu-Val-Asp-AFC) and fluorescence (excitation 400 nm and emission 505 nm) was determined. Caspase units were defined as pmols of substrate cleaved per minute per milligram extract protein.

Results and Discussion

Figure 3A:
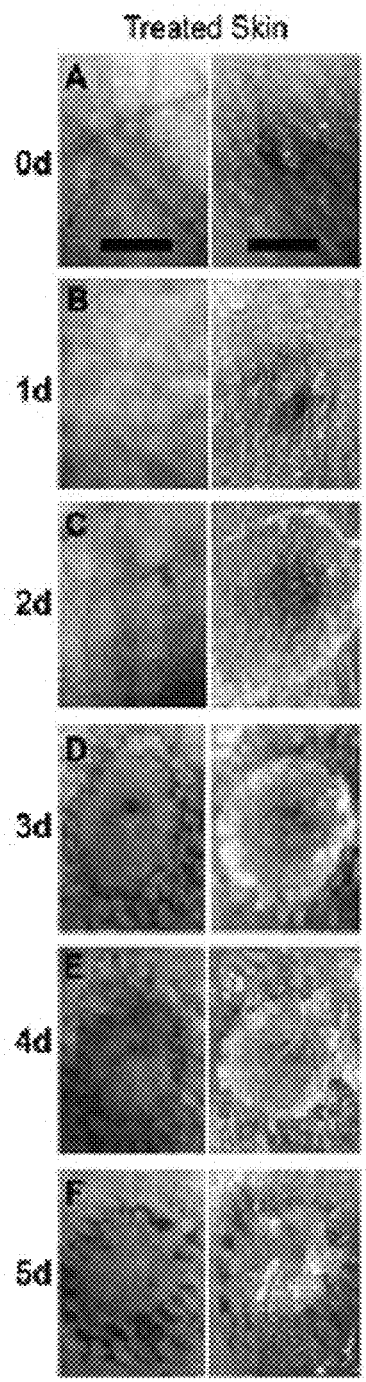
FIGS. 3A-3C show the typical response of skin and melanoma to one or two applications of 100 pulses using a 5-needle array electrode on mouse #56. Each matched pair of photos represents an in situ transillumination of the skin on the left and a surface view on the right. Numbers on the far left indicate the number of days after pulsing at which all three matched pairs to the right were photographed. (A-F) The typical response of normal skin to 100 pulses (300 ns long, 20 kV/cm, 0.5 Hz) delivered on day 0. Small superficial erosion in B grows in C-E and indicates loss of some or all epidermis. (H-M) The electrode array was inserted into this tumor on day 0 but no pulses were delivered. (O-T) 100 pulses (300 ns long, 20 kV/cm) were delivered at 0.5 Hz on day 0 and day 1. Necrosis evident on day two becomes more intense over time. Scale bars A-T: 1 mm and all photos in a given row are at the same magnification.
Figure 3B:
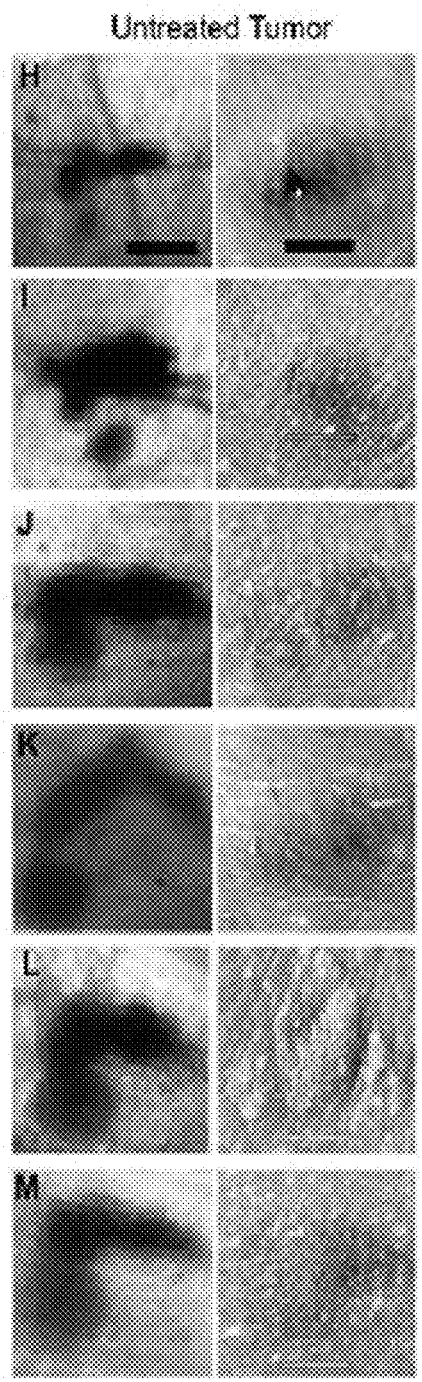
Figure 3C:
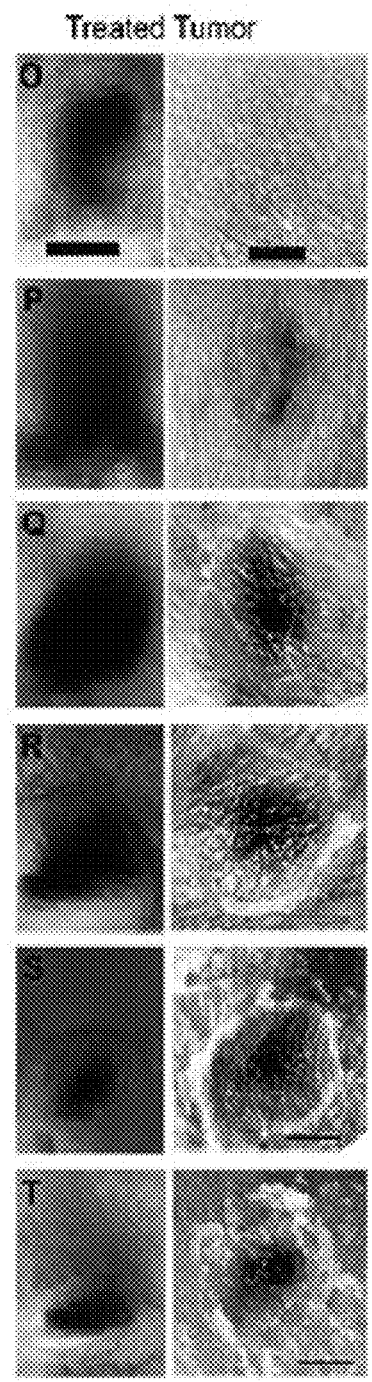

The electric field was applied using two different electrode configurations. The first was a 5-needle electrode array (FIG. 2A) in which the needles penetrated about 2 mm into the mouse skin. In 59 mice, the central needle was placed in the center of the melanoma to be treated and the outer 4 needles were outside of the boundary edges of the melanoma. This electrode array exhibits a sharply non-uniform field with field lines parallel to the surface of the skin and strongest near the center electrode (FIG. 2B). When the needle array is inserted into a melanoma for a couple of minutes and removed, the melanoma continues to grow normally (FIG. 3B Panels H-M). However, if 100 pulses (8 kV, 300 ns. 0.5 Hz) are administered to the needle array prior to removal, the melanoma begins to shrink within 2 days (FIG. 3C Panels O-T). Blood flow to the tumor is disrupted after pulsing as red blood cells leak out of capillaries surrounding the tumor (FIG. 3P). Local blood flow usually does not recover for about two weeks. Two days after pulsing, the stratum corneum shows signs of necrosis and hemorrhage with accompanying superficial erosion of the epidermis and the tumor becomes darker (FIG. 3C Panel Q). This suggests that in addition to the tumor cells, the epidermal cells of the skin between the electrodes that differentiate into the stratum corneum are damaged by the 300 ns pulsed electric field (nsPEF). These results were confirmed by treating skin regions where there were no melanomas and observing similar superficial erosion over the same time period (FIG. 3A Panels A-F). Insulating the upper shaft of the needles that come into contact with the epidermis may reduce this damage.

This tumor response is dependent on both field strength and pulse number. If the field strength is cut in half by using a 4 kV pulse (average field of 10 kV/cm), there is no significant difference between the growth rates of treated and control tumors (FIG. 4A). This holds true for the application of both 10 and 100 pulses (FIG. 4B). The pulse number dependence is more evident for the 8 kV pulses (20 kV/cm field) where the response is stronger for 100 pulses than it is for 10 (FIGS. 4 C, D) and even stronger when two treatments of 100 pulses are given (FIG. 4E). Under this latter condition, the tumors shrink by about 75% within 8 days.

The second electrode configuration used involved placing the tumor between two parallel plates (FIG. 6A). The electric field between two parallel plates is uniform except at the edges, so that all cells between the plates will be exposed to the same field strength. These electrodes were used when treating 48 mice by lifting a fold of skin containing the melanoma away from the mouse and placing it between the electrodes in such a way that the entire tumor was positioned between the plates. Thus the field was oriented perpendicular to the skin surface rather than parallel to it as with the needle electrodes. The distance between the plates was typically 0.5-1 mm, depending on tumor thickness. Based on our previous results with needle electrodes, a field strength of 40 kV/cm was employed and the typical response to nanosecond pulses with this electrode configuration is illustrated in FIG. 5. One difference between the two electrode types is the appearance of the skin beginning two days after treatment. A black scab appears on the stratum corneum in the pulsed region and it remains for about two weeks as the stratum corneum is regenerated (FIG. 5B). Histological examination of this scab indicates that it is composed of clotted red blood cells. Tumors typically shrank by 90% within 2 weeks following four 100-pulse treatments using plate electrodes (3 on day 0 and 1 on day 4) (FIG. 6B). However after about two weeks of regression, all tumors began to grow again and we sacrificed the mice at that time so that we could fix and section the tumors for histology.

Multiple Treatments Result in Complete Tumor Remission—

Tumors were treated with a second 3-day series of 100 pulses when they stopped shrinking two to three weeks after the initial treatment. In three such cases, total remission of the tumor was observed and one example is shown in FIG. 7. Within two months of the initial treatment, the melanoma was undetectable by transillumination, ultrasound or serial section histological investigation.

nsPEF Raises Tumor Temperature Only 3° C.—

The energy delivered to the tissue between 5 mm plates is 0.2 J if the plate separation is 1 mm. Given the specific heat of water, this should only increase the tissue temperature by two to three degrees. This temperature increase was directly measured by inserting a very small thermocouple into the tumor and confirmed that the maximum temperature reached after 100 pulses was 33° C. (FIG. 8). This is ten degrees lower than the minimum temperature required for hyperthermia effects so it is very unlikely that effects of nsPEF on tumor growth are due to hyperthermia.

Targets and Potential Mechanisms for nsPEF Effects—

Two immediate changes in the tumor have been identified following the application of the electric field pulses that may be responsible for the tumor regression: (a) tumor cell nuclei rapidly become pyknotic and (b) blood stops flowing to the tumor. Untreated tumor cells exhibited lightly staining pleomorphic nuclei and abundant cytoplasm containing finely dispersed melanin granules (FIG. 9). Treated tumors exhibited densely staining, shrunken nuclei and dyshesion of individual cells with coarse intracellular melanin granules as well as aggregated extracellular melanin granules in the widened interstitial spaces. The tumor cell nuclei shrink by 54% within a few minutes after pulsing and by 68% within three hours. No further nuclear shrinkage occurred during the subsequent two weeks as the tumor decreased in size by 90% (FIG. 9E). Some of the tumor nuclei elongate along the electric field axis but this is not always observed. The tumor cells themselves also shrink over this time period because the cell density is higher by one and three hours posttreatment. The nuclear pyknosis that follows pulse application occurs faster than any previously observed pyknotic response (S. M. Albarenque, K. Doi (2005) *Exp. Mol. Pathol.* 78:144-149) and may result from either electrode-formation [18] or the direct electric field interaction with cytoskeletal elements associated with the cell's nuclear lamina to generate the nuclear elongation and shrinking (P. K. Wong, W. Tan, C. M. Ho (2005) *J. Biomech.* 38:529-535; Y. Gruenbaum, A. Margalit, R. D. Goldman, D. K. Shumaker, K. L. Wilson (2005) *Nat. Rev. Mol. Cell Biol.* 6:21-31).

The second major change that is immediately obvious is a reduction in blood flow to the tumor. Both transillumination and power Doppler ultrasound reconstructions indicate that the blood flow has stopped within about 15 min after pulsing (FIG. 10). Histology confirms that red blood cells are found scattered within and around the melanoma tumor. This implies that the local blood vessels become leaky and red blood cells escape into the surrounding tissues. Blood flow to the tumor does not normally recover for about two weeks. If blood flow returns, the tumor usually begins growing again. This lack of blood flow to the melanoma certainly contributes to its regression.

Any changes in the classical apoptosis marker, caspase activity, were also determined. The activity of caspases was measured using a fluorogenic substrate Ac-DEVD-AFC at 0, 3, 6 and 9 hours after treatment with 100 pulses in three experiments. The only time at which caspase activity appeared to increase was at 3 hours when there was a 2.6-fold increase in mean activity. However, this small change failed the normality t-test and the Mann-Whitney Rank Sum test indicating that it was not a statistically significant difference (p=0.1). It is possible that an apoptosis program is initiated, but since apoptosis is an energy-requiring process, the interruption of the blood supply to the tumor may prevent completion of the apoptosis mechanism.

Previously Reported Changes in DNA Post-nsPEF—

The rapid pyknosis that was observed suggests that the cellular DNA could be a direct or indirect target of nsPEF. The precise mechanism by which this damage is induced is not clear. Two possible mechanisms include activation of DNases in the apoptotic pathway or mechanically induced DNA breakage. A typical tumor cell nucleus measuring 10 μm in diameter will experience a voltage gradient of about 40 V across itself during each pulse. This electric field is large enough to cause rapid electromechanical deformation of the nucleus generating a mechanical shock to the DNA attached to the nuclear envelope that could damage the DNA.

These nsPEF stimulate murine melanomas to self-destruct by triggering rapid pyknosis and reducing blood flow without significant increases in caspase activity. A reduction in blood flow to tumors has also been observed following electrochemotherapy but does not occur until 24 h after treatment when the bleomycin entry had destroyed the endothelial cells (G. Sersa, M. Cemazar, C. S. Parkins, D. J. Chaplin (1999) *Eur. J. Cancer* 35:672-677). In contrast, nsPEF requires no drugs to achieve this dramatic reduction in tumor blood flow. This cellular response to a new nanosecond time domain of pulsed electric field application is both novel and deadly. While this technique has yet to be tested on humans, it may have advantages over the surgical removal of skin lesions because incisions through the dermis often leave scarring on the healed skin. NsPEF affects the tumor without disrupting the dermis so that scarring is less likely. NsPEF should also be effective on other tumor types located deeper in the body where a catheter electrode is guided to the tumor. This highly localized and drug-free physical technique offers a promising new therapy for tumor treatment.

Long-Term Study of the Application of nsPEFs to Induce Complete Tumor Regression—

The study began with 27 mice (13 experimentals and 14 controls) with one melanoma tumor each. Each experimental mouse was treated with 300 pulses with a duration of 300 ns and an amplitude of 40 kV/cm. All treated tumors began shrinking within 24 hr and continued to shrink for two weeks. Eleven of them began to grow again at that point and were treated a second time with the same pulse parameters. Two of the tumors continued to shrink and are no longer detectable. Three of the 11 tumors that were treated twice were treated a third time about 3 weeks after the second treatment. All 13 experimental tumors are exhibiting complete remission (FIG. 11). In contrast, 11 of the 14 controls had to be euthanized when their tumors grew to 1.3 cm as specified in our protocol. Three of the controls stopped growing prior to reaching this size and are still alive. These mice were six months old when the B16 melanoma cells were injected and their immune response may be strong enough to keep the melanomas under control in these three mice. At 120 days since the first treatment for 9 of the experimental mice, and 90 days since the first treatment for 4 of them, these mice remained tumor-free.

Treatment of UV-Induced Melanomas—

An important question involves the response of a skin tumor that has arisen from native epidermal cells rather than carcinoma cells that have been injected into the animal. Preliminary studies show that two transgenic mice with UV-induced melanomas on their backs have responded well to a treatment of 300 pulses, 300 ns, 40 kV/cm. Obtaining transillumination data was not possible due to the dark pigmentation of these mice. However, both ultrasound and surface images exhibit the rapid shrinkage of these melanomas (FIG. 12).

Two Needle-Insertion Electrode Configuration—

Besides using a "coaxial" configuration, as shown in FIG. 2, two-needle systems have also been used for melanoma treatment with success. A melanoma tumor where two-needles were placed sequentially along the tumor has caused the tumor to shrink considerably in a 24 hour period as shown in FIG. 13. The advantage of a two- or more-unit needle system in a linear array, rather than a coaxial array, is the fact that the needles do not need to be inserted directly into the tumor, and consequently, possible contamination and/or metastasis is avoided.

The foregoing detailed description includes many specific details. The inclusion of such detail is for the purpose of illustration only and should not be understood to limit the invention. In addition, features in one embodiment may be combined with features in other embodiments of the invention. Various changes may be made without departing from the scope of the invention as defined in the following claims. In addition, all non-priority patents and other references cited herein are indicative of the level of skill in the art and are hereby incorporated by reference in their entirety.

What is claimed is:

1. A method for inducing tumor regression, the method comprising:
    coating a tissue overlying the tumor with a composition that reduces flashover during pulse field application; and
    applying at least one nsPEF to the tumor, wherein the at least one nsPEF has a pulse duration of at least about 1 nanosecond and no more than about 1 microsecond and an electric field pulse strength of at least about 10 kV/cm and no more than about 350 kV/cm.

2. The method of claim 1, wherein the at least one nsPEF is applied through a catheter electrode.

3. The method of claim 1, wherein the electric field pulse strength is between about 20 kV/cm and about 45 kV/cm.

4. The method of claim 1, wherein the at least one nsPEF has a pulse duration of at least about 300 nanoseconds.

5. The method of claim 1, the method comprising varying pulse duration based on at least one or more of the following: tissue type, cell type, or desired treatment.

6. The method of claim 1, wherein the tumor comprises cancer cells.

7. The method of claim 1, wherein the tumor is located in a skin tissue.

8. The method of claim 7, wherein the tumor comprises melanoma cells.

9. The method of claim 1, wherein the tumor comprises one or a combination of any of the following: fat, bone, skin, vascular cells, muscle, cartilage.

10. The method of claim 1, whereby said method is carried out in situ.

11. The method of claim 1, wherein the applying is performed using a pulse generator.

12. The method of claim 1, the method comprising using plate electrodes, needles, or needle arrays to deliver the at least one nsPEF to the tumor.

13. The method of claim 12, wherein the coating step comprises using the plate electrodes, the needles, or the needle arrays coated with the composition that reduces flashover.

14. The method of claim 1, wherein said method is repeated one or more times.

15. A method for selectively initiating apoptosis in skin cells in a tissue comprising:
    coating a skin tissue with a composition that reduces flashover during pulse field application; and
    applying at least one nsPEF to the skin tissue, wherein the at least one nsPEF has a pulse duration of at least about 1 nanosecond and no more than about 1 microsecond and an electric field pulse strength of at least about 10 kV/cm and no more than about 350 kV/cm.

16. The method of claim 15, wherein the at least one nsPEF is applied through a catheter electrode.

17. The method of claim 15, the method comprising varying pulse duration based on at least cell type or desired treatment.

18. The method of claim 15, wherein the skin tissue comprises cancer cells.

19. The method of claim 15, wherein the coating comprises using plate electrodes, needles, or needle arrays coated with the composition that reduces flashover.

20. The method of claim 15, wherein the skin tissue comprises melanoma cells.

21. A method for inhibiting blood flow in a tissue, the method comprising:
    coating the tissue with a composition that reduces flashover during pulse field application; and
    applying at least one nsPEF to the tissue, wherein the at least one nsPEF has a pulse duration of at least about 1 nanosecond and no more than about 1 microsecond and an electric field pulse strength of at least about 10 kV/cm and no more than about 350 kV/cm.

22. The method of claim 21, the method comprising guiding a catheter electrode to the tissue.

23. The method of claim 21, wherein the at least one nsPEF has an electric field pulse strength of at least about 20 kV/cm and no more than about 45 kV/cm.

24. The method of claim 21, comprising applying at least 100 nsPEFs to the tissue.

25. The method of claim 21, wherein the tissue comprises one or a combination of any of the following: fat, bone, skin, vascular cells, muscle, cartilage.

* * * * *